United States Patent [19]
Tasaka et al.

[11] Patent Number: 5,919,799
[45] Date of Patent: Jul. 6, 1999

[54] IMIDAZOTHIAZOLE COMPOUND

[75] Inventors: Shigeyuki Tasaka; Akira Kiue, both of Saitama, Japan

[73] Assignee: Nikken Chemicals Co., Ltd., Tokyo, Japan

[21] Appl. No.: 08/913,276

[22] PCT Filed: Mar. 13, 1996

[86] PCT No.: PCT/JP96/00626

§ 371 Date: Sep. 9, 1997

§ 102(e) Date: Sep. 9, 1997

[87] PCT Pub. No.: WO96/28454

PCT Pub. Date: Sep. 19, 1996

[30] Foreign Application Priority Data

Mar. 13, 1995 [JP] Japan .................................. 7-079330

[51] Int. Cl.$^6$ ........................ C07D 513/04; A61K 31/425
[52] U.S. Cl. ........................ 514/322; 514/338; 514/366; 546/199; 546/271; 548/151
[58] Field of Search .............. 548/151; 546/271, 546/199; 514/366, 338, 322

[56] References Cited

U.S. PATENT DOCUMENTS 3,579,530  5/1971  Dewar .

FOREIGN PATENT DOCUMENTS

| | | |
|---|---|---|
| 2699920 | 7/1994 | France . |
| 1127822 | of 0000 | Japan . |
| 1127823 | of 0000 | Japan . |
| 2138221 | of 0000 | Japan . |
| 2240081 | of 0000 | Japan . |
| 240383 | of 0000 | Japan . |
| 4235983 | of 0000 | Japan . |
| 5117235 | of 0000 | Japan . |
| 565487 | of 0000 | Japan . |
| 5740492 | of 0000 | Japan . |
| 63152116 | of 0000 | Japan . |
| 63152117 | of 0000 | Japan . |
| 63329341 | of 0000 | Japan . |
| 692391 | of 0000 | Japan . |
| 692401 | of 0000 | Japan . |
| 56-138196 | 10/1981 | Japan . |
| 56138196 | 10/1981 | Japan . |
| 57-149288 | 9/1982 | Japan . |
| 1-319487 | 12/1989 | Japan . |
| 1-319488 | 12/1989 | Japan . |
| 2-178289 | 7/1990 | Japan . |
| 2699920 | 1/1994 | Japan . |

OTHER PUBLICATIONS

Patent Abstracts of Japan, vol. 6, No. 257 (C–140), 16 Dec. 1982 & JP 57 149288 A (Yamanouchi Seiyaku KK), 14 Sep. 1982.

Patent Abstracts of Japan, vol. 6, No. 110 (C–109), 22 Jun. 1982 & JP 57 040492 A (Yamanouchi Pharmaceut Co Ltd), 6 Mar. 1982.

Paten Abstracts of Japan, vol. 16, No. 584 (C–1013), 24 Dec. 1992 & JP 04 235983 A (Mitssui Toatsu Chem Inc).

A.–N. El–Shorbagi et al.; Chemical and Pharmaceutical Bulletin, vol. 37, No. 11, 1989, pp. 2971–5, XP002062481.

*Primary Examiner*—Robert Gerstl
*Attorney, Agent, or Firm*—Christie, Parker & Hale, LLP

[57] ABSTRACT

An imidazothiazole compound having the formula (A):

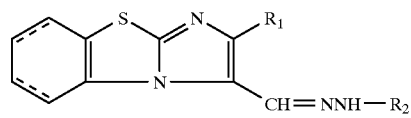

(A)

wherein $R_1$ is a phenyl or napthyl which may have a substituent, $R_2$ is an acyl, and the two bonds at dotted line portions may or may not exist simultaneously, or a pharmacologically acceptable salt thereof and an agent for overcoming resistance to an anti-neoplastic agent or an enhancer for the effect of an anti-neoplastic agent comprising said compound or a pharmacologically acceptable salt thereof as an active ingredient.

18 Claims, No Drawings

IMIDAZOTHIAZOLE COMPOUND

TECHNICAL FIELD

The present invention relates to a novel imidazothiazole compound having an action in overcoming resistance to an anti-neoplastic agent or an action in enhancing the effect of an anti-neoplastic agent, more specifically relates to a tetrahydroimidazo-benzothiazole or imidazobenzothiazole compound.

BACKGROUND ART

At the present time, in chemotherapy for cancer, "acquired resistance" where the cancer suppressing effect is lost during treatment is becoming a problem. Multidrug resistance where resistance is exhibited against various types of anti-neoplastic agents is becoming an important issue. As a method for overcoming this multidrug resistance, it has been reported that co-administration of the anti-neoplastic agent and some calcium antagonists (1,4-dihydropyridine compounds such as Nicardipine) is effective. (Cancer Res., 41, 1967–1972 (1981), Cancer and Chemotherapy, vol. 11, 750–759 (1984)).

Further, Japanese Unexamined Patent Publication (Kokai) No. 2-40383, Japanese Unexamined Patent Publication (Kokai) No. 2-240081, Japanese Examined Patent Publication (Kokoku) No. 6-92391, Japanese Examined Patent Publication (Kokoku) No. 6-92401, Japanese Unexamined Patent Publication (Kokai) No. 5-117235, and Japanese Unexamined Patent Publication (Kokai) No. 2-138221 describe that a 1,4-dihydropyridine compound has an action overcoming resistance to anti-neoplastic agents. Further, recently, there are reports on quinoline or indole derivatives having a similar action in overcoming resistance to anti-neoplastic agents (see Japanese Unexamined Patent Publication (Kokai) No. 4-235983 and Japanese Unexamined Patent Publication (Kokai) No. 5-43544).

On the other hand, as imidazothiazole derivatives, 2-phenylimidazo[2,1-b]benzothiazole derivatives have an immunomodulating action, and therefore, patent applications have been filed as an anti-allergenic, an anti-rheumatic, and an anti-asthmatic drugs (see Japanese Unexamined Patent Publication (Kokai) No. 56-138196, Japanese Unexamined Patent Publication (Kokai) No. 57-40492, and Japanese Unexamined Patent Publication (Kokai) No. 57-149288). Further, patent applications have been filed for 2-methylimidazo[2,1-b]benzothiazole and 5,6,7,8-tetrahydro-2-methylimidazo[2,1-b]benzothiazole derivatives as an anti-neoplastic agent or brain enhancers (see Japanese Unexamined Patent Publication (Kokai) No. 1-319487, Japanese Unexamined Patent Publication (Kokai) No. 1-319488, Japanese Unexamined Patent Publication (Kokai) No. 2-178289, Japanese Unexamined Patent Publication (Kokai) No. 2-306918, and Japanese Unexamined Patent Publication (Kokai) No. 2-306917).

Further, as imidazothiazole derivatives, 2,3,5,6-tetrahydro-6-phenylimidazo[2,1-b]thiazole (Tetramisole) is known to exhibit an immunosuppressive action and an anticancer action (see U.S. Pat. No. 3,579,530 (1971)).

However, no report has been made concerning the action of a tetrahydroimidazobenzothiazole or imidazobenzothiazole compound in overcoming resistance to anti-neoplastic agents.

DISCLOSURE OF INVENTION

The present inventors synthesized large numbers of tetrahydroimidazobenzothiazole or imidazobenzothiazole compounds and screened these compounds broadly for the existence of co-acting effects thereof with anti-neoplastic agents. As a result, we discovered that imidazothiazole compounds having the following formula (A) have an action of remarkably increasing the sensitivity of cancer cells to anti-neoplastic agents, in particular the sensitivity of cancer cells having acquired resistance to anti-neoplastic agents. Further, they learned that these compounds have the effect of prolonging the period of survival of tumor bearing animals through the administration thereof in combination with anti-neoplastic agents and further are low in toxicity, whereby the present invention has been completed.

That is, in accordance with the present invention, there is provided an imidazothiazole compound having the formula (A):

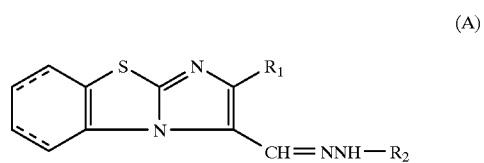

(wherein, $R_1$ is a phenyl group or a naphthyl group which may have a substituent, $R_2$ is an acyl group, and the bonds at two dotted line portions may or may not exist simultaneously), or a pharmacologically acceptable salt thereof and an agent for overcoming resistance to anti-neoplastic agent or an agent for enhancing the effect of anti-neoplastic agent comprising said compound or a pharmacologically acceptable salt thereof as an active ingredient.

BEST MODE FOR CARRYING OUT THE INVENTION

The present invention will now be explained in further detail below.

The compounds having the formula (A) specifically include the compounds having the following formula (I) and formula (II):

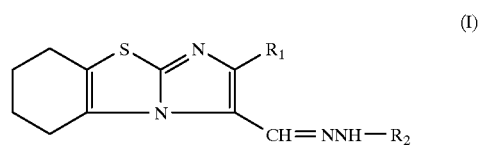

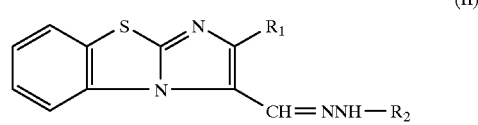

In the compounds having the formula (I) or formula (II), as the phenyl or naphthyl which may have a substituent for $R_1$, a phenyl or naphthyl which may be substituted with a nitro, halogen atom, a lower alkoxy such as methoxy or ethoxy, a $C_1$ to $C_3$ lower alkyl such as a methyl or ethyl or a dialkylamino such as a dimethylamino or diethylamino or phenyl may be mentioned.

Among these, as the preferable groups for $R_1$, phenyl group or naphthyl which may be substituted with a nitro, fluoro, methoxy, dimethylamino, or a phenyl, more specifically, a phenyl, 3-nitrophenyl, 4-nitrophenyl, 4-fluorophenyl, 4-N,N-dimethylaminophenyl, biphenyl, naphthyl, etc. may be mentioned.

As $R_2$, an acyl may be mentioned. As a preferable acyl, a benzoyl, pyridylcarbonyl, piperidylcarbonyl, etc. which may have a substituent such as a $C_1$ to $C_3$ lower alkyl or lower alkoxy such as a methoxy or ethoxy, particularly a benzoyl, pyridylcarbonyl, or piperidylcarbonyl substituted with a $C_1$ to $C_5$ lower alkyl such as a methyl, ethyl, propyl, or isopropyl, a benzyl, etc. at the N-position, specifically, a benzoyl, 3-pyridylcarbonyl, N-methyl-3-piperidylcarbonyl, N-propyl-3-piperidylcarbonyl, N-isopropyl-3-piperidylcarbonyl, N-benzyl-3-piperidylcarbonyl, etc. may be mentioned.

As the pharmacologically acceptable salts of the compounds having the formula (I) or (II), inorganic salts formed from hydrochloric acid, hydrobromic acid, sulfuric acid, bisulfurous acid, phosphoric acid, etc. and organic salts formed from formic acid, acetic acid, citric acid, fumaric acid, gluconic acid, lactic acid, maleic acid, succinic acid, tataric acid, methanesulfonic acid, benzenesulfonic acid, toluenesulfonic acid, etc. may be exemplified.

Specific examples of preferred compounds will be shown below.

(Compound 1) 5,6,7,8-tetrahydro-2-phenyl-3-(3-pyridylcarbonylaminoiminomethyl)imidazo[2,1-b]benzothiazole (Compound 2) 5,6,7,8-tetrahydro-2-biphenyl-3-(3-pyridylcarbonylaminoiminomethyl)imidazo[2,1-b]benzothiazole (Compound 3) 5,6,7,8-tetrahydro-2-(3-nitrophenyl)-3-(3-pyridylcarbonylaminoiminomethyl)imidazo[2,1-b]benzothiazole (Compound 4) 5,6,7,8-tetrahydro-2-(3,4,5-trimethoxyphenyl)-3-(3-pyridylcarbonylaminoiminomethyl)imidazo[2,1-b]benzothiazole (Compound 5) 5,6,7,8-tetrahydro-2-phenyl-3-(N-methyl-3-piperidylcarbonylaminoiminomethyl)imidazo[2,1-b]benzothiazole (Compound 6) 5,6,7,8-tetrahydro-2-(4-nitrophenyl)-3-(3-pyridylcarbonylaminoiminomethyl)imidazo[2,1-b]benzothiazole (Compound 7) 5,6,7,8-tetrahydro-2-(4-N,N-dimethylaminophenyl)-3-(3-pyridylcarbonylaminoiminomethyl)imidazo[2,1-b]benzothiazole (Compound 8) 5,6,7,8-tetrahydro-2-phenyl-3-(benzoylaminoiminomethyl)imidazo[2,1-b]benzothiazole (Compound 9) 5,6,7,8-tetrahydro-2-phenyl-3-[N-benzyl-3-piperidylcarbonylaminoiminomethyl]imidazo[2,1-b]benzothiazole (Compound 10) 5,6,7,8-tetrahydro-2-(4-nitrophenyl)-3-[N-methyl-3-piperidylcarbonylaminoiminomethyl]imidazo[2,1-b]benzothiazole hydrochloride (Compound 11) 5,6,7,8-tetrahydro-2-biphenyl-3-[N-methyl-3-piperidylcarbonylaminoiminomethyl]imidazo[2,1-b]benzothiazole hydrochloride (Compound 12) 5,6,7,8-tetrahydro-2-phenyl-3-[N-propyl-3-piperidylcarbonylaminoiminomethyl]imidazo[2,1-b)benzothiazole hydrochloride (Compound 13) 5,6,7,8-tetrahydro-2-phenyl-3-[N-isopropyl-3-piperidylcarbonylaminoiminomethyl]imidazo[2,1-b]benzothiazole hydrochloride (Compound 14) 2-phenyl-3-[3-pyridylcarbonylaminoiminomethyl]imidazo[2,1-b]benzothiazole (Compound 15) 2-phenyl-3-[N-methyl-3-piperidylcarbonylaminoiminomethyl]imidazo[2,1-b]benzothiazole hydrochloride (Compound 16) 2-phenyl-3-[N-propyl-3-piperidylcarbonylaminoirainomethyl]imidazo[2,1-b]benzothiazole hydrochloride (Compound 18) 5,6,7,8-tetrahydro-2-(5-fluorophenyl)-3-[N-methyl-3-piperidylcarbonylaminoiminomethyl]imidazo[2,1-b]benzothiazole hydrochloride (Compound 19) 5,6,7,8-tetrahydro-2-(2-napthyl)-3-[N-methyl-3-piperidylcarbonylaminoiminomethyl]imidazo[2,1-b]benzothiazole hydrochloride The imidazothiazole compounds shown by formula (I) or formula (II) according to the present invention can be produced by well-known methods. The method for producing an imidazothiazole compound having the formula (I) will be shown below by way of example. That is, first, dimethylformamide and phosphorus oxychloride are allowed to react with a compound having the following formula (III) to produce the aldehyde having formula (IV) (Vilsmeier-Haack reaction). The aldehyde having formula (IV) and an acid hydrazide having formula (V) are then allowed to react under an acidic condition (Method A) or allowed to react under a basic condition (Method B).

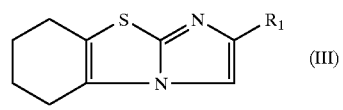

(III)

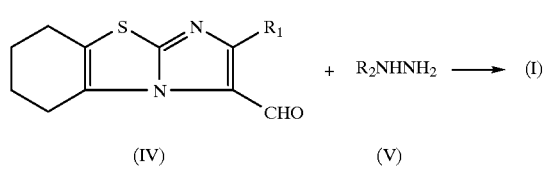

(IV)  (V)

wherein, $R_1$ and $R_2$ are as defined above.

The starting compounds used for these production processes are either easily available known compounds or can be easily produced, if necessary, by a person skilled in the art.

The compounds having the formula (I) obtained by these methods may be isolated and purified by known treatment means (for example, extraction, chromatography, recrystallization, etc.).

The compounds having the formula (II) may be produced by the same methods as above, except for using a compound of imidazo[2,1-b]benzothiazole substituted with $R_1$ at its 2-position as a starting compound.

The compounds according to the present invention exhibit an action for enhancing the effect of an anti-neoplastic agent and further exhibit an action overcoming the resistance to an anti-neoplastic agent for adriamycin resistant cancers and vincristine resistant cancers and exhibit an action prolonging the survival time of cancerous animals by the administration thereof in combination with an anti-neoplastic agent, so are useful as an agent for overcoming resistance to an anti-neoplastic agent or an enhancer for the effect of an anti-neoplastic agent.

When the compounds according to the present invention are used as agents for overcoming resistance to an antineoplastic agent or an enhancer for the effect of an antineoplastic agent, they may be administered by a suitable oral or non-oral method of administration. As the form of oral administration, tablets, granules, capsules, pills, dispersions, solutions, etc. may be exemplified. Further, as the form of non-oral administration, injections, suppositories, etc. may be exemplified. These preparations may be prepared according to ordinary methods using compounds of the present invention or pharmacologically acceptable salts thereof and ordinary preparation carriers.

For example, in the case of oral administration, the preparations can be prepared into the desired form using excipients such as lactose, gluclose, corn starch, and sucrose, disintegrators such as calcium carboxymethyl cellulose and hydroxypropyl cellulose, lubricants such as calcium stearate, magnesium stearate, talc, polyethylene glycol, and hydrogenated oil, binding agents such as hydroxypropyl cellulose, hydroxypropylmethyl cellulose, carboxymethyl cellulose, polyvinyl alcohol, gelatin, and gum arabic, humectants such as glycerol and ethylene glycol, and, in addition, if necessary, surfactants, corrigents, etc.

Further, in the case of a non-oral drug, diluents such as water, ethanol, glycerol, propylene glycol, polyethylene glycol, agar, and tragacanth gum may be used and, if necessary, solubilization aids, buffer agents, preservatives, flavors, coloring agents, etc. may be used.

When formulating the compounds of the present invention as drugs for overcoming resistance to an anti-neoplastic agent or an enhancer for the effect of an anti-neoplastic agent, the dosage, as the compound of the present invention, is per adult, in the case of oral administration, 5 to 1000 mg per day, preferably 5 to 200 mg, and in the case of non-oral administration, 1 to 500 mg per day, preferably 1 to 200 mg. The desired effect of treatment can be expected by administration divided into one to three dosages per day.

EXAMPLES

The Synthesis Examples, Preparation Examples, and Test Examples of the compounds according to the present invention will be exemplified below, but the present invention is of course not limited to these Examples.

Synthesis Examples

The Synthesis Examples will be shown below. The NMR data is shown in Table 1 as the main signal of $^1$H-NMR measured by a DMSO-$d_6$ solution.

Example 1 a) Synthesis of 5,6,7,8-tetrahydro-2-phenyl-3-formylimidazo[2,1-b]benzothiazole 3.35 g of 5,6,7,8-tetrahydro-2-phenylimidazo[2,1-b]benzothiazole was suspended in 20 ml of dimethylformamide. To the resultant mixture, 3 ml of phosphorus oxychloride was added dropwise at 0° C. over 10 minutes. The solution was gradually returned to room temperature, then heated and stirred at 60° C. for 3 hours, poured onto an aqueous sodium carbonate solution, then extracted with chloroform. The solvent was distilled off, the residue was then recrystallized from ethanol to obtain the desired substance in an amount of 2.31 g (yield of 82.0%) (melting point:150–150.5° C.).

b) Synthesis of 5,6,7,8-tetrahydro-2-phenyl-3-(3-pyridylcarbonylaminoiminomethyl)imidazo[2,1-b]bibenzothiazole (Compound 1)

(Method A)

0.28 g of 5,6,7,8-tetrahydro-2-phenyl-3-formylimidazo[2,1-b]benzothiazole and 0.15 g of nicotinohydrazide were stirred over night in 20 ml of a 0.1N hydrochloric acid-ethanol solution at room temperature. The precipitated crystal was obtained by filtration. Ammonia solution was added to the crystals, then extracted with chloroform. The extract was washed with water and dried, then the solvent was distilled off and the residue was crystallized from ethanol to obtain the desired substance in an amount of 0.33 g (yield of 82.5%).

(Method B)

0.28 g of 5,6,7,8-tetrahydro-2-phenyl-3-formylimidazo[2,1-b]benzothiazole, 0.15 g of nicotinohydrazide, and 0.1 g of potassium hydroxide were heated and stirred in 20 ml of methanol at 90° C. for 1.5 hours. After cooling, the solvent was distilled off under reduced pressure and the residue was extracted with chloroform. The extract was washed with water and dried, then the solvent was distilled off and the residue was crystallized from ethyl acetate to obtain the desired substance in an amount of 0.35 g (yield of 87.5%).

Example 2

Synthesis of 5,6,7,8-tetrahydro-2-biphenyl-3-(3-pyridylcarbonylaminoiminomethyl) tetrahydroimidazo[2,1-b]benzothiazole (Compound 2)

5,6,7,8-tetrahydro-2-biphenylimidazo[2,1-b]benzothiazole was treated in the same way as in Example 1a) to synthesize 5,6,7,8-tetrahydro-2-biphenyl-3-formylimidazo(2,1-b]benzothiazole (melting point: 167.5–168° C.)

Next, 0.31 g of 5,6,7,8-tetrahydro-2-biphenyl-3-formylimidazo[2,1-b]benzothiazole, 0.15 g of nicotinohydrazide, and 0.1 g of potassium hydroxide were heated and stirred in 20 ml of methanol at 90° C. for 1.5 hours. After cooling, the solvent was distilled off under reduced pressure and the residue was extracted with chloroform. The extract was washed with water and dried, then the solvent was distilled off and the residue was crystallized from ethanol to obtain the desired substance in an amount of 0.38 g (yield of 79.6%).

Example 3

Synthesis of 5,6,7,8-tetrahydro-2-(3-nitrophenyl)-3-(3-pyridylcarbonylaminoiminomethyl)imidazo[2,1-b]benzothiazole (Compound 3)

5,6,7,8-tetrahydro-2-(3-nitrophenyl)imidazo[2,1-b]benzothiazole was treated in the same way as in Example 1a) to synthesize 5,6,7,8-tetrahydro-2-(3-nitrophenyl)-3-formylimidazo[2,1-b]benzothiazole (melting point:163–163.5° C.).

Next, 0.33 g of 5,6,7,8-tetrahydro-2-(3-nitrophenyl)-3-formylimidazo[2,1-b]benzothiazol, 0.15 g of nicotinohydrazide, and 0.1 g of potassium hydroxide were heated and stirred in 20 ml of methanol at 90° C. for 1.5 hours. After cooling, water was added and the desired substance was obtained in an amount of 0.21 g (yield of 46.7%).

Example 4

Synthesis of 5,6,7,8-tetrahydro-2-(3,4,5-trimethoxyphenyl)-3-(3-pyridylcarbonylaminoiminomethyl)imidazo[2,1-b]benzothiazole (Compound 4)

5,6,7,8-tetrahydro-2-(3,4,5-trimethoxyphenyl)imidazo[2,1-b]benzothiazole was treated in the same way as in Example 1a) to synthesize 5,6,7,8-tetrahydro-2-(3,4,5-trimethoxyphenyl)-3-formylimidazo[2,1-b]benzothiazole (melting point: 187.5–188° C.).

Next, 0.37 g of 5,6,7,8-tetrahydro-2-(3,4,5-trimethoxyphenyl)-3-formylimidazo[2,1-b]benzothiazole, 0.15 g of nicotinohydrazide, and 0.1 g of potassium hydroxide were heated and stirred in 20 ml of methanol at 90° C. for 1.5 hours. After cooling, the solvent was distilled off under reduced pressure and the residue was extracted with chloroform. The extract was washed with water and dried, then the solvent was distilled off and the residue was crystallized from methanol to obtain the desired substance in an amount of 0.40 g (yield of 81.6%).

Example 5

Synthesis of 5,6,7,8-tetrahydro-2-phenyl-3-(N-methyl-3-piperidylcarbonylaminoiminomethyl)imidazo[2,1-b]benzothiazole (Compound 5)

0.30 g of 5,6,7,8-tetrahydro-2-phenyl-3-formylimidazo[2,1-b]benzothiazole, 0.15 g of N-methylnipecotinohydrazide, and 0.1 g of potassium hydroxide were heated and stirred in 20 ml of methanol at 90° C. for 1.5 hours. After cooling, the solvent was distilled off under reduced pressure and the residue was extracted with chloroform. The extract was washed with water and dried, then the solvent was distilled off and the residue was crystallized from ethyl acetate to obtain the desired substance (syn:anti=about 1:1) in an amount of 0.24 g (yield of 55.8%).

Example 6

Synthesis of 5,6,7,8-tetrahydro-2-(4-nitrophenyl)-3-(3-pyridylcarbonylaminoiminomethyl)imidazo[2,1-b]benzothiazole (Compound 6)

5,6,7,8-tetrahydro-2-(4-nitrophenyl)imidazo[2,1-b]benzothiazole was treated in the same way as in Example 1a) to synthesize 5,6,7,8-tetrahydro-2-(4-nitrophenyl)-3-formylimidazo[2,1-b]benzothiazole (melting point: 237.5–238° C.).

Next, 0.33 g of 5,6,7,8-tetrahydro-2-(4-nitrophenyl)-3-formylimidazo[2,1-b]benzothiazole, 0.15 g of nicotinohydrazide, and 0.1 g of potassium hydroxide were heated and stirred in 20 ml of methanol at 90° C. for 1.5 hours. After cooling, the solvent was distilled off under reduced pressure and the residue was extracted with chloroform. The extract was washed with water and dried, then the solvent was distilled off and the residue was crystallized from methanol to obtain the desired substance in an amount of 0.25 g (yield of 55.6%).

Example 7

Synthesis of 5,6,7,8-tetrahydro-2-(4-N,N-dimethylaminophenyl)-3-(3-pyridylcarbonylaminoiminomethyl)imidazo[2,1-b]benzothiazole (Compound 7)

5,6,7,8-tetrahydro-2-(4-N,N-dimethylaminophenyl)imidazo[2,1-b]benzothiazole was treated in the same way as in Example 1a) to synthesize 5,6,7,8-tetrahydro-2-(4-N,N-dimethylaminophenyl)-3-formylimidazo[2,1-b]benzothiazole (melting point:179–180° C.).

Next, 0.33 g of 5,6,7,8-tetrahydro-2-(4-N,N-dimethylaminophenyl)-3-formylimidazo[2,1-b]benzothiazole, 0.15 g of nicotinohydrazide, and 0.1 g of potassium hydroxide were heated and stirred in 20 ml of methanol at 90° C. for 1.5 hours. After cooling, the solvent was distilled off under reduced pressure and the residue was extracted with chloroform. The extract was washed with water and dried, then the solvent was distilled off and the residue was crystallized from methanol to obtain the desired substance in an amount of 0.24 g (yield of 54.1%).

Example 8

Synthesis of 5,6,7,8-tetrahydro-2-phenyl-3-(benzoylaminoiminomethyl)imidazo[2,1-b]benzothiazole (Compound 8)

0.28 g of 5,6,7,8-tetrahydro-2-phenyl-3-formylimidazo[2,1-b]benzothiazole and 0.15 g of benzohydrazide were stirred over night in 20 ml of a 0.1N hydrochloric acid-ethanol solution at room temperature and the precipitated crystal obtained by filtration. The crystals were dissolved in water and the solution was made alkaline by ammonia solution, then extracted by chloroform. The extract was washed with water and dried, then the solvent was distilled off and the residue was crystallized from ethyl acetate to obtain the desired substance in an amount of 0.35 g (yield of 84.0%).

Example 9

Synthesis of 5,6,7,8-tetrahydro-2-phenyl-3-[N-benzyl-3-piperidylcarbonylaminoiminomethyl]imidazo[2,1-b]benzothiazole (Compound 9)

0.30 g of 5,6,7,8-tetrahydro-2-phenyl-3-formylimidazo[2,1-b]benzothiazole, 0.15 g of N-benzylnipecotohydrazide, and 0.1 g of potassium hydroxide were heated and stirred in 20 ml of methanol at 90° C. for 1.5 hours. After cooling, the solvent was distilled off under reduced pressure and the residue was extracted with chloroform. The extract was washed with water and dried, then the solvent was distilled off and the residue was crystallized from ethyl acetate to obtain the desired substance (syn:anti=about 1:1) in an amount of 0.24 g (yield of 55.8%).

Example 10

Synthesis of 5,6,7,8-tetrahydro-2-(4-nitrophenyl)-3-[N-methyl-3-piperidylcarbonylaminoiminomethyl]imidazol[2,1-b]benzothiazole hydrochloride (Compound 10)

0.30 g of 5,6,7,8-tetrahydro-2-(4-nitrophenyl)-3-formylimidazo[2,1-b]benzothiazole, 0.15 g of N-methylnipecotohydrazide, and 0.1 g of potassium hydroxide were heated and stirred in 20 ml of methanol at 90° C. for 1.5 hours. After cooling, the resultant mixture was extracted with chloroform. The extract was washed with water and dried, then the solvent was distilled off and the residue was crystallized from ethyl acetate to obtain 0.20 g (yield of 46.8%). This product was dissolved in 0.1N HCl-EtOH, and the insolubles were filtered out. Then the remainder was condensed and acetone was added to obtain the desired compound (syn:anti=about 1:1) in an amount of 0.13 g.

Example 11

Synthesis of 5,6,7,8-tetrahydro-2-biphenyl-3-[N-methyl-3-piperidylcarbonylaminoiminomethyl]imidazo[2,1-b]benzothiazole hydrochloride (Compound 11)

0.36 g of 5,6,7,8-tetrahydro-2-biphenyl-3-formylimidazo[2,1-b]benzothiazole, 0.15 g of N-methylnipecotohydrazide, and 0.1 g of potassium hydroxide were heated and stirred in 20 ml of methanol at 90° C. for 2 hours. After cooling, the resultant mixture was extracted with chloroform. The extract was washed with water and dried, then the solvent was distilled off and the residue was crystallized from ethyl acetate to obtain 0.30 g (yield of 60.4%). This product was dissolved in 0.1N HCl-EtOH, and the insolubles were filtered out. Then the remainder was condensed and acetone was added to obtain the desired compound (syn:anti=about 1:1) in an amount of 0.26 g.

Example 12

Synthesis of 5,6,7,8-tetrahydro-2-phenyl-3-[N-propyl-3-piperidylcarbonylaminoiminomethyl] imidazo[2,1-b]benzothiazole hydrochloride (Compound 12)

0.25 g of 5,6,7,8-tetrahydro-2-phenyl-3-formylimidazo[2,1-b]benzothiazole and 0.20 g of N-propylnipencotohydrazide were dissolved in 10 ml of 0.1N HCl-EtOH. Then allowed at room temperature for 2 days and left over night in a refrigerator to obtain the desired compound (syn:anti=about 1:1) in an amount of 0.28 g (yield of 71.8%).

Example 13

Synthesis of 5,6,7,8-tetrahvdro-2-phenyl-3-[N-isopropyl-3-piperidylcarbonylaminoiminomethyl] imidazo[2,1-b]benzothiazole hydrochloride (Compound 13)

0.25 g of 5,6,7,8-tetrahydro-2-phenyl-3-formylimidazo[2,1-b]benzothiazole and 0.20 g of N-methylnipencotohydrazide were dissolved in 10 ml of HCl-EtOH. Then allowed to react at room temperature for 2 days and left over night in a refrigerator to obtain the desired compound (syn:anti=about 1:1) in an amount of 0.25 g (yield of 64.1%).

Example 14

Synthesis of 2-phenyl-3-[3-pyridylcarbonylaminoiminomethyl]imidazo[2,1-b] benzothiazole (Compound 14)

0.28 g of 2-phenyl-3-formylimidazo[2,1-b]benzothiazole, 0.15 g of N-methylnipecotohydrazide, and 0.1 g of potassium hydroxide were heated and stirred in 20 ml of methanol at 90° C. for 6 hours. After cooling, the desired substance was obtained in an amount of 0.27 g (yield of 68.0%).

Example 15

Synthesis of 2-phenyl-3-[N-methyl-3-piperidylcarbonylaminoiminomethyl]imidazo[2,1-b] benzothiazole hydrochloride (Compound 15)

0.50 g of 2-phenyl-3-formylimidazo[2,1-b]benzothiazole, 0.30 g of N-methylnipecotohydrazide, and 0.1 g of potassium hydroxide were heated and stirred in 20 ml of methanol at 90° C. for 2 hours. After cooling, the insolubles were removed, then the solution was extracted with chloroform, washed with water and dried. The solvent was distilled off and the residue was crystallized from ethyl acetate to obtain 0.66 g (yield of 88.0%). This compound was dissolved in 0.1N HCl-EtOH, the insolubles were filtered out, the remainder was condensed, and acetone was added to obtain the desired compound in an amount of 0.38 g.

Example 16

Synthesis of 2-phenyl-3-[N-propyl-3-piperidylcarbonylaminoimino-methyl]imidazo[2,1-b]benzothiazole hydrochloride (Compound 16)

0.50 g of 2-phenyl-3-formylimidazo[2,1-b]benzothiazole, 0.30 g of N-propylnipecotohydrazide, and 0.1 g of potassium hydroxide were heated and stirred in 20 ml of methanol at 90° C. for 5 hours. After cooling, the insolubles were removed, then the solution was extracted with chloroform, washed with water and dried. Then the solvent was distilled off and the residue was crystallized from ether to obtain 0.40 g (yield of 50.0%). This compound was dissolved in 0.1N HCl-EtOH, the insolubles were filtered out, the remainder was condensed, and acetone was added to obtain the desired compound in an amount of 0.30 g.

Example 17

Synthesis of 5,6,7,8-tetrahydro-2-(3,4,5-trimethoxyphenyl)-3-[N-methyl-3-piperidylcarbonylaminoiminomethyl]imidazo[2,1-b] benzothiazole (Compound 17)

0.50 g of 5,6,7,8-tetrahydro-2-(3,4,5-trimethoxyphenyl)-3-formylimidazo[2,1-b]benzothiazole, 0.30 g of N-methylnipecotohydrazide, and 0.1 g of potassium hydroxide were heated and stirred in 20 ml of methanol at 90° C. for 1 hour. After cooling, the resultant mixture was extracted with chloroform. The extract was washed with water and dried, then the solvent was distilled off and the residue was crystallized from ethyl acetate to obtain the desired compound (syn:anti=about 1:1) in an amount of 0.35 g (yield of 50.9%).

Example 18

Synthesis of 5,6,7,8-tetrahvdro-2-(4-fluorophenyl)-3-[N-methyl-3-piperidylcarbonylaminoiminomethyl] imidazo[2,1-b]benzothiazole (Compound 18)

0.50 g of 5,6,7,8-tetrahydro-2-(4-fluorophenyl)-3-formylimidazo[2,1-b]benzothiazole, 0.30 g of N-methylnipecotohydrazide, and 0.1 g of potassium hydroxide were heated and stirred in 20 ml of methanol at 90° C. for 1 hour. After cooling, the resultant mixture was extracted with chloroform. The extract was washed with water and dried, then the solvent was distilled off and the residue was crystallized from ethyl acetate ester to obtain the desired compound (syn:anti=about 1:1) in an amount of 0.38 g (yield of 52.1%).

Example 19

Synthesis of 5,6,7,8-tetrahydro-2-(2-napthyl)-3-[N-methyl-3-piperidylcarbonylaminoiminomethyl] imidazo[2,1-b]benzothiazole (Compound 19)

0.30 g of 5,6,7,8-tetrahydro-2-(2-napthyl)-3-formylimidazo[2,1-b]benzothiazole, 0.20 g of N-methylnipecotohydrazide, and 0.1 g of potassium hydroxide were heated and stirred in 20 ml of methanol at 90° C. for 2 hours. After cooling, the resultant mixture was extracted with chloroform. The extract was washed with water and dried, then the solvent was distilled off and the residue was crystallized from ethyl acetate ester to obtain the desired compound (syn:anti=about 1:1) in an amount of 0.35 g (yield of 81.4%).

TABLE 1

| | | Formula (I) | | Formula (II) |

General formula: Formula (I) - tetrahydrobenzothiazole fused imidazole with R₁ at 2-position and CH=NNH-R₂ at 3-position; Formula (II) - benzothiazole fused imidazole with R₁ at 2-position and CH=NNH-R₂ at 3-position.

| Example | Formula | R₁ | R₂ | $^1$H—NMR(($\delta$: ppm)(Solvent: DMSO-$d_6$) |
|---|---|---|---|---|
| 1 | I | phenyl | 3-pyridyl-C(O)- | 1.83(4H, m) 2.72(2H, m) 3.27(2H, m) 8.61(1H, s) 7.41–9.07(9H, m)11.94(1H, s) |
| 2 | I | 4-biphenylyl | 3-pyridyl-C(O)- | 1.85(4H m) 2.74(2H, m) 3.28(2H, m) 8 68(1H, s) 7.39–9.08(13H, m) 11.98(1H, s) |
| 3 | I | 3-nitrophenyl | 3-pyridyl-C(O)- | 1.86(4H, m) 2.75(2H, m) 3.17(2H, m) 8.62(1H, s) 7.56–9.07(8H, m) 12.01(1H, s) |
| 4 | I | 3,4,5-trimethoxyphenyl | 3-pyridyl-C(O)- | 1.85(4H, m) 2.73(2H, m) 3.26(2H, m) 3.71(3H, s) 3.87(6H, s) 7.02(2H, s) 8.67(1H, s) 7.55–9.05 (4H,m) 12.02(1H, s) |
| 5 | I | phenyl | 1-methyl-3-piperidyl-C(O)- | 1.81(4H, m) 2.22(2H, m) 2.72(3H, s) 3.05(1H, m) 3.17(1H, m) 8.29(0.5H, 5) 8.35(0.5H, 5) 7.39–7.68(5H, m) |
| 6 | I | 4-nitrophenyl | 3-pyridyl-C(O)- | 1.86(4H, m) 2.74(2H, m) 3.16(2H, m) 8.72(1H, s) 7.58–9.08(8H, m) 12.00(1H, s) |
| 7 | I | 4-(dimethylamino)phenyl | 3-pyridyl-C(O)- | 1.83(4H m) 2.71(2H, m) 2.95(6H, s) 3.29(2H, m) 8.57(1H, s) 6.80–9.07(8H, m) 11.89(1H, s) |
| 8 | I | phenyl | 3-pyridyl-C(O)- | 1.84(4H, m) 2.74(2H, m) 3.28(2H, m) 8.65(1H, s) 7.47–7.92(10H, m) 11.82(1H, s) |

TABLE 1-continued
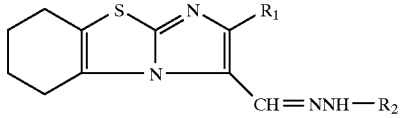
Formula (I)
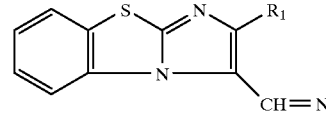
Formula (II)
| Example | General formula | $R_1$ | $R_2$ | $^1$H—NMR(($\delta$: ppm)(Solvent: DMSO-$d_6$) |
|---|---|---|---|---|
| 9 | I | 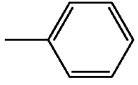 | 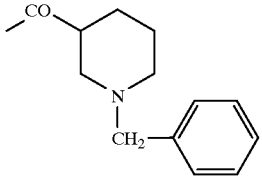 | 1.81(4H, m) 2.72(2H, m) 3.17(2H, m) 4:24(2H, s) 7.39–7.68(10H, m) 8.35(1H, s) |
| 10 | I | 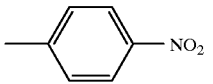 | 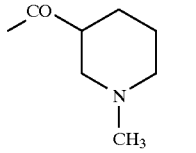 | 1.82(4H, m) 2.73(1.5H, s) 2.74(1.5H, s) 8.33(0.5, s) 8.61(0.5H, s) 7.95–8.33(4H, m) |
| 11 | I | 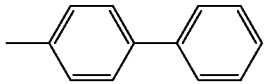 | 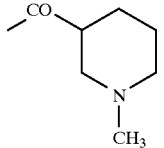 | 1.82(4H, m) 2.72(1.5H, s) 2.73(1.5H, s) 8.38(0.5H, s) 8.49(0.5H, s) 7.40–7.82(9H, m) |
| 12 | I | 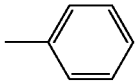 | 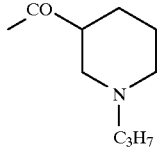 | 0.90(3H, t) 1.81(4H, m) 1.99(2H, m) 3.43(2H, t) 8.31(0.5H, s) 8.42(0.5H, s) 7.41–7.69(5H, m) |
| 13 | I | 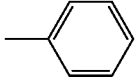 | 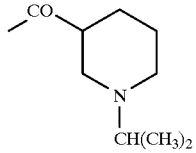 | 1.29(6H, d) 1.81(4H, m) 8.31(0.5H, s) 8.44(0.5H, s) 7.40–7.69(5H, m) |
| 14 | II | 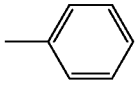 | 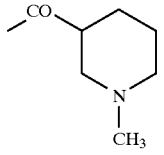 | 8.73(1H, s) 7.48–10.05(13H, m) |
| 15 | II | 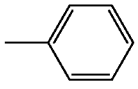 | 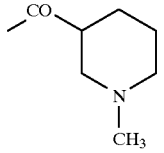 | 2.76(3H, d) 8.53(1H, s) 7.46–9.88(9H, m) |

TABLE 1-continued

General formula: Formula (I) / Formula (II) — thiazole-fused imidazole compounds with CH=NNH—R$_2$ substituent

| Example | Formula | R$_1$ | R$_2$ | $^1$H—NMR(($\delta$: ppm)(Solvent: DMSO-d$_6$) |
|---|---|---|---|---|
| 16 | II | phenyl | 3-piperidinyloxycarbonyl (N-C$_3$H$_7$) | 0.90(3H, t) 2.01(2H, m) 3.06(2H, t) 8.55(1H, s) 7.45–9.90(9H, m) |
| 17 | I | 3,4,5-trimethoxyphenyl (OCH$_3$, OCH$_3$, OCH$_3$) | 3-piperidinyloxycarbonyl (N-CH$_3$) | 1.82(4H, m) 2.72(3H, s) 3.84(3H, s) 3.86(6H, s) 6.82(1H, s) 7.03(1H, s) 8.30(0.5H, s) 8.50(0.5H, s) |
| 18 | I | 4-fluorophenyl | 3-piperidinyloxycarbonyl (N-CH$_3$) | 1.81(4H, m) 2.72(3H, s) 2.33(2H, m) 3.02(1H, m) 3.14(1H, m) 7.22–7.78(4H, m) 8.30(0.5H, s) 8.36(0.5, s) |
| 19 | I | 6-methylnaphthalen-2-yl | 3-piperidinyloxycarbonyl (N-CH$_3$) | 1.82(4H, m) 2.36(2H, m) 2.72(3H, s) 3.06(1H, m) 3.15(1H, m) 7.53–8.13(7H, m) 8.39(0.5H, s) 8.53(0.5H, s) |

Preparation Examples

Example 20 (Preparation of Tablets)

| | |
|---|---|
| Compound of present invention (Compound 1) | 25 g |
| Lactose | 62 g |
| Corn starch | 40 g |
| Hydroxypropyl cellulose | 2 g |
| Magnesium stearate | 1 g |

The above compound of the present invention, lactose, and corn starch were mixed to become homogeneous, then a 5 W/V% ethanol solution of hydroxypropyl cellulose was added and the mixture was mixed and granulated. The granules were graded by passing them through a 16 mesh sieve, then were formed into tablets by an ordinary method to obtain tablets having a weight per tablet of 130 mg, a diameter of 7 mm, and a content of the active ingredient of 25 mg.

Test Examples

Test Example 1

In Vitro Test of Effect of Suppression of Proliferation of Cancer Cells by Co-Administration with Doxorubicin Human epipharynx cancer derived cancer KB cells (sensitive cells) and their multidrug resistant clones VJ-300 cells (resistant cells) were used as test cells. As the incubation solution, an Eagle MEM medium (made by Nissui Seiyakusha) containing 10% fetal calf serum (made by Flow Laboratories Co.) and 0.292 mg/ml L-glutamine (made by Flow Laboratories Co.) was used. The action overcoming resistance to an anti-neoplastic agent and effect in enforcing the effect of an anti-neoplastic agent obtained through co-administration of the anti-neoplastic agent doxorubicin (adriamycin, ADM) and the test compounds were tested as follows:

The test cells were suspended in the incubation medium and adjusted to a cell density of about 200 cells/ml. 2 ml portions of the cell suspension were placed in petri dishes and incubated in a carbon dioxide gas incubator (5% CO$_2$, 95% air) at 37° C. for 24 hours. Next, predetermined concentrations of aqueous ADM solutions and dimethyl sulfoxide (DMSO) solutions of predetermined concentrations of the test compounds were added into 5 to 10 $\mu$l portions, then incubation was continued for 7 days. After the end of the incubation, the samples were fixed by methanol, Giemsa staining was performed, the number of colonies in each dish was counted, and a volume reaction curve was prepared. This was used to calculate the ADM concentration at a 50% cell survival rate ($LD_{50}$) and judge the action overcoming resistance to an anti-neoplastic agent and effect in enhancing the effect of an anti-neoplastic agent.

The $LD_{50}$ concentration of ADM in the ADM control group for KB cells was shown as the resistance degree "1" and the other $LD_{50}$ concentrations were indexed against this to calculate the resistance degrees. The results are shown in Table 2. In Table 2, ADM alone (control) is the group administered ADM alone, ADM+Compound 1 is the group co-administered ADM and Compound 1 (1 µg /ml) and so on down to ADM+Compound 19 which is the group co-administered ADM and Compound 19 (1 µg /ml).

TABLE 2

|  | Resistance at ADM | |
|---|---|---|
|  | KB | VJ-300 |
| ADM alone (Control) | 1 | 46.7 |
| ADM + Compound 1 | 0.82 | 7.5 |
| ADM + Compound 2 | 0.87 | 5.5 |
| ADM + Compound 3 | 0.19 | 6.8 |
| ADM + Compound 4 | 0.82 | 8.9 |
| ADM + Compound 5 | 0.53 | 1.7 |
| ADM + Compound 6 | 0.27 | 10.6 |
| ADM + Compound 7 | 0.91 | 6.7 |
| ADM + Compound 9 | 0.43 | 1.5 |
| ADM + Compound 10 | 0.43 | 1.7 |
| ADM + Compound 11 | 0.49 | 1.1 |
| ADM + Compound 12 | 0.48 | 0.58 |
| ADM + Compound 13 | 0.63 | 0.79 |
| ADM + Compound 14 | 0.95 | 4.7 |
| ADM + Compound 15 | 0.81 | 1.5 |
| ADM + Compound 16 | 1.02 | 1.7 |
| ADM + Compound 17 | 0.97 | 9.8 |
| ADM + Compound 18 | 0.99 | 1.1 |
| ADM + Compound 19 | 1.00 | 0.93 |

Test Example 2

In Vitro Test of Effect of Suppression of Proliferation of Cancer Cells by Co-Administration with Vincristine This test was performing by a method similar to Test Example 1 using vincristine (VCR) as the anti-neoplastic agent. A volume reaction curve was prepared and the resistance calculated. The results are shown in Table 3 and Table 4. In the Tables, VCR alone (control) is the group administered VCR alone, VCR+Compound 1 is the group co-administered VCR and Compound 1(1 µg /ml) and so on down to VCR+Compound 16 which is the group co-administered VCR and Compound 16 (1 µg/ml).

TABLE 3

|  | Resistance with VCR | |
|---|---|---|
|  | KB | VJ-300 |
| VCR alone (Control) | 1 | 306.6 |
| VCR + Compound 1 | 0.69 | 3.3 |
| VCR + Compound 2 | 0.30 | 1.6 |
| VCR + Compound 3 | 0.24 | 2.7 |
| VCR + Compound 4 | 0.60 | 20.9 |
| VCR + Compound 5 | 0.36 | 1.2 |
| VCR + Compound 8 | 0.55 | 3.5 |

TABLE 4

|  | Resistance with VCR | |
|---|---|---|
|  | KB | VJ-300 |
| VCR alone (Control) | 1 | 843.1 |
| VCR + Compound 9 | 0.29 | 2.5 |
| VCR + Compound 10 | 0.25 | 8.7 |
| VCR + Compound 11 | 0.10 | 1.3 |
| VCR + Compound 12 | 0.54 | 1.3 |
| VCR + Compound 13 | 0.58 | 2.0 |
| VCR + Compound 14 | 0.72 | 4.0 |
| VCR + Compound 15 | 0.88 | 3.1 |
| VCR + Compound 16 | 0.81 | 2.6 |

Test Example 3

In Vivo Test of Effect of Suppression of Proliferation of Cancer Cells by Co-Administration With Anti-Neoplastic Agent Effect of Overcoming Resistance to Anti-Neoplastic Agent in Vincristine (VCR) Resistant Murine Leukemia Cell Bearing Mice (a) $10^6$ VCR resistant murine leukemic (P388/VCR) cells were transplanted intraperitoneally to groups of six $CDF_1$ male mice. The compound of the present invention (10 or 100 mg/kg) was suspended in 0.5% sodium carboxymethyl cellulose containing 0.1% Tween 80, while the VCR (100 µg/kg) was dissolved in physiological saline. These were each administered intraperitoneally over 5 days and the mice observed to find the days of survival and the rate of prolongation of life with respect to the control (T/C). The effect in overcoming resistance to an anti-neoplastic agent (T/V) was found from the following formula:

Effect in overcoming resistance to anti-neoplastic agent (T/V%)= (Rate of prolongation of life when co-administering VCR and compound of present invention (T/C%))/(Rate of prolongation of life by VCR alone (T/C))×100

The results are shown in Table 5. In Table 5, "Control" is the non-administered group, VCR alone is the group administered just VCR (100 µg /kg), VCR+Compound 1 is the group co-administered VCR (100 µg /kg) and Compound 1 (100 mg/kg) and so on to VCR+Compound 14* which is the group co-administered VCR (100 µg /kg) and Compound 14 (10 mg/kg).

TABLE 5

|  | Days of survival (days) | Rate of prolongation of life (T/C %) | Effect overcoming resistance (T/V %) |
|---|---|---|---|
| Control | 10.45 | 100 | — |
| VCR alone | 11.08 | 106 | 100 |
| VCR + Compound 1 | 12.33 | 118 | 111 |
| VCR + Compound 2 | 12.67 | 121 | 114 |
| VCR + Compound 4 | 13.28 | 127 | 120 |
| VCR + Compound 5 | 14.38 | 138 | 130 |
| VCR + Compound 8 | 12.00 | 115 | 108 |
| VCR + Compound 14* | 13.67 | 131 | 124 |

*Compound 14 was administered in a dosage of 10 mg/kg for the test. The others were all 100 mg/kg.

(b) Separately, groups of six $CDF_1$ male mice were intravenously given transplants of $1.2 \times 10^5$ VCR resistant murine leukemia (P388/VCR) cells. The compound of the present invention (20 or 40 mg/kg) was dissolved in 0.01N hydrochloric acid. Etoposide (VP-16, 3 mg/kg) was dissolved in a physiological saline solution. These were administered intravenously for five days and the days of survival were found. In the same way as (a), the rate of prolongation of life with respect to the control (T/C) and the effect in overcoming the resistance to an anti-neoplastic agent (T/V) were found. The results are shown in Table 6. In Table 6, the control is the non-administered group, VP-16 alone is the group administered VP-16 (3 mg/kg) and VP-16+Compound 5 is the group co-administered VP-16 (3 mg/kg) and Compound 5 (40 mg/kg) and so on to VP-16+Compound 16 which is the group co-administered VP-16 (3 mg/kg) and Compound 16 (40 mg/kg).

TABLE 6

|  | Days of survival (days) | Rate of prolongation of life (T/C %) | Effect overcoming resistance (T/V %) |
| --- | --- | --- | --- |
| Control | 10.3 | 100 | — |
| VP-16 alone | 11.2 | 109 | 100 |
| VP-16 + Compound 5 | 14.0 | 136 | 125 |
| VP-16 + Compound 10* | 12.0 | 117 | 107 |
| VP-16 + Compound 11 | 13.0 | 126 | 116 |
| VP-16 + Compound 12 | 13.2 | 128 | 118 |
| VP-16 + Compound 15 | 13.0 | 126 | 116 |
| VP-16 + Compound 16 | 12.7 | 123 | 113 |

*Compound 10 was administered in a dosage of 20 mg/kg. The others were all 40 mg/kg.

Test Example 4
Acute Toxicity Test
(a) Animals used: ICR male mice (Charles River Japan), 7 to 8 weeks old, were used three to a group.
Test method: The compound of the present invention was suspended in 0.5% sodium carboxymethyl cellulose(CMC-Na) containing 0.1% Tween 80. This was administered intraperitoneally from 2000 mg/kg at a rate of ½ to 125 mg/kg and from 125 mg/kg at a rate of $1/\sqrt{2}$ to 31.3 mg/kg until deaths of three animals per group were no longer seen. The survival of the animals was examined up to 7 days after administration, then the Van Der Wearder area method was used to calculate the $LD_{50}$ value. The test results are shown below.

| Compound 1 | not less than 2000 mg |
| --- | --- |
| Compound 2 | not less than 2000 mg |
| Compound 5 | 604 mg |

(b) Groups of five mice were tested in the same way as in (a) except that the drug was administered intraperitoneally from 1000 mg by a rate of $1/\sqrt{2}$ until 250 mg/kg. The test results are shown below.

| Compound 12 | 592 mg |
| --- | --- |
| Compound 15 | not less than 1000 mg |

Industrial Applicability

The imidazobenzothiazole and tetrahydroimidazobenzothiazole compounds according to the present invention increase the effect of an anti-neoplastic agent by co-administration with the same. This effect is particularly remarkably against clones obtaining resistance to an anti-neoplastic agent. For example, as clear from Table 3, VJ-300 cells, that is, multidrug resistant clones of human epipharynx cancer derived KB cells require use of 306.6 times the concentration of an anti-neoplastic agent to obtain the same effect (50% resistant cancer cell survival rate) as with cells not acquiring resistance to an anti-neoplastic agent while the same effect can be obtained with a concentration of 1.2 times that level when using Compound 5 (1 μg/ml) of the present invention.

Further, the compounds of the present invention are low in toxicity and proved effective both in in vitro and in vivo tests, so are useful as drugs for overcoming resistance to an anti-neoplastic agent or an agent for enhancing the effect of an anti-neoplastic agent.

We claim:
1. An imidazothiazole compound having the formula (A):

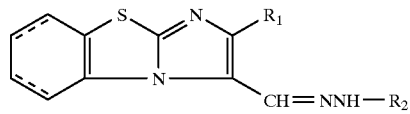

(A)

wherein $R_1$ is a phenyl or naphthyl which may have a substituent, $R_2$ is an acyl, and the two bonds at dotted line portions may or may not exist simultaneously, or a pharmacologically acceptable salt thereof.

2. An imidazothiazole compound or a pharmacologically acceptable salt thereof as claimed in claim 1, wherein $R_1$ is a phenyl or naphthyl which may be substituted with nitro, halogen atom, lower alkoxy, lower alkyl, dialkylamino, or phenyl.

3. An imidazothiazole compound or a pharmacologically acceptable salt thereof as claimed in claim 1, wherein $R_1$ is a phenyl or naphthyl of which phenyl may be substituted with nitro, halogen atom, lower alkoxy, lower alkyl, dialkylamino, or phenyl.

4. An imidazothiazole compound or a pharmacologically acceptable salt thereof as claimed in claim 1, wherein $R_1$ is a phenyl, nitrophenyl, fluorophenyl, trimethoxyphenyl, dimethylaminophenyl, or biphenyl.

5. An imidazothiazole compound or a pharmacologically acceptable salt thereof as claimed in claim 1, wherein $R_1$ is a phenyl.

6. An imidazothiazole compound or a pharmacologically acceptable salt thereof as claimed in any one of claims 1 to 5, wherein $R_2$ is a benzoyl, pyridylcarbonyl or piperidylcarbonyl, which may have a substituent.

7. An imidazothiazole compound or a pharmacologically acceptable salt thereof as claimed in claim 6, wherein $R_2$ is a benzoyl, pyridylcarbonyl, or a piperidylcarbonyl substituted with a lower alkyl or benzyl at the N-position thereof.

8. An imidazothiazole compound or a pharmacologically acceptable salt thereof as claimed in claim 7, wherein $R_2$ is a benzoyl, 3-pyridylcarbonyl, N-methyl-3-piperidylcarbonyl, N-benzyl-3-piperidylcarbonyl, N-propyl-3-piperidylcarbonyl, or N-isopropyl-3-piperidylcarbonyl.

9. An imidazothiazole compound as claimed claim 1, wherein the compound has the following formula (I):

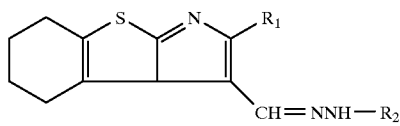

or a pharmacologically acceptable salt thereof.

10. An imidazothiazole compound as claimed in claim 1, wherein the compound has the following formula (II):

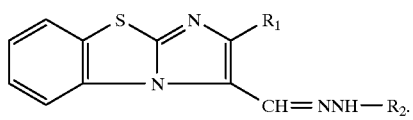

or a pharmacologically acceptable salt thereof.

11. An agent for overcoming resistance to an anti-neoplastic agent comprising, as an active ingredient, an imidazothiazole compound or a pharmacologically acceptable salt thereof according to claim 1.

12. An enhancer for the effect of anti-neoplastic agent comprising, as an active ingredient, an imidazothiazole compound or a pharmacologically acceptable sat thereof according to claim 1.

13. An imidazothiazole compound or a pharmacologically acceptable salt thereof as claimed in claim 9, wherein $R_1$ is a phenyl or naphthyl which may be substituted with nitro, halogen atom, lower alkoxy, lower alkyl, dialkylamino, or phenyl, and $R_2$ is a benzoyl, pyridylcarbonyl or piperidylcarbonyl, which may have a substituent.

14. An imidazothiazole compound or a pharmacologically acceptable salt thereof as claimed in claim 10, wherein $R_1$ is a phenyl or naphthyl which may be substituted with nitro, halogen atom, lower alkoxy, lower alkyl, dialkylamino, or phenyl, and $R_2$ is a benzoyl, pyridylcarbonyl or piperidylcarbonyl, which may have a substituent.

15. An agent for overcoming resistance to an anti-neoplastic agent comprising, as an active ingredient, an imidazothiazole compound or a pharmacologically acceptable salt thereof according to claim 13.

16. An agent for overcoming resistance to an anti-neoplastic agent comprising, as an active ingredient, an imidazothiazole compound or a pharmacologically acceptable salt thereof according to claim 14.

17. An enhancer for effect of anti-neoplastic agent comprising, as an active ingredient, an imidazothiazole compound or a pharmacologically acceptable salt thereof according to claim 13.

18. An enhancer for effect of anti-neoplastic agent comprising, as an active ingredient, an imidazothiazole compound or a pharmacologically acceptable salt thereof according to claim 14.

* * * * *

UNITED STATES PATENT AND TRADEMARK OFFICE
CERTIFICATE OF CORRECTION

PATENT NO. : 5,919,799
DATED : July 6, 1999
INVENTOR(S) : Shigeyuki Tasaka; Akira Kiue It is certified that error appears in the above-identified patent and that said Letters Patent is hereby corrected as shown below:

Title page,
Item [56] References Cited, OTHER PUBLICATIONS, replace "Paten Abstracts of Japan, vol. 16 ..." with -- Patent Abstracts of Japan, vol. 16 -- and insert -- Cancer Res., 41, 1967-1972 (1981), Cancer and Chemotherapy, vol. 11, 750-759 (1984). --.

Column 4,
Line 5, replace that portion of the compound reading "piperidylcarbonylaminoirainomethyl" with -- piperidylcarbonylaminoiminomethyl --.

Column 5,
Line 65, replace that portion of the compound reading "bibenzothiazole" with -- benzothiazole --.

Column 6,
Line 29, replace that portion of the compound reading "formylimidazo(2, 1-b] benzothiazole" with -- formylimidazo[2, 1-b]benzothiazole --.

Column 9,
Line 21, replace "N-propylnipencotohydrazide" with -- N-propylnipeccotohydrazide --.
Line 28, replace that portion of the compound reading "tetrahvdro" with -- tetrahydro --.
Line 35, replace that portion of the compound reading "N-methylnipencotodydrazide" with -- N-methylnipecotodydrazide --.

Column 10,
Line 38, replace that portion of the compound reading "tetrahvdro" with -- tetrahydro --.

Column 12,
Example 2, replace "1.85(4H m)" with -- 1.85(4H,m) --.
Example 5, replace "8.35(0.5H, 5) with -- 8.35(0.5H, s) --.
Example 8, the formula under $R_2$ should read --

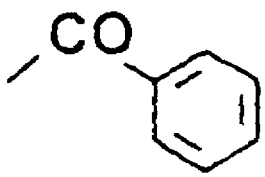

--

UNITED STATES PATENT AND TRADEMARK OFFICE
CERTIFICATE OF CORRECTION

PATENT NO. : 5,919,799
DATED : July 6, 1999
INVENTOR(S) : Shigeyuki Tasaka; Akira Kiue It is certified that error appears in the above-identified patent and that said Letters Patent is hereby corrected as shown below:

Column 14,
Example 9, replace "4:24(2H, s)" with -- 4.24 (2H, s) --.
Example 14, the formula under $R_2$ should read --

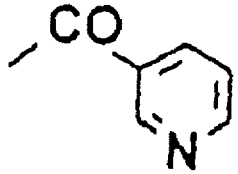

Column 17,
Line 46, replace "performing" with -- performed --.

Column 19,
Line 66, replace "remarkably" with -- remarkable --.

Column 21,
Line 29, replace "sat" with -- salt --.

Signed and Sealed this

Eighth Day of January, 2002

JAMES E. ROGAN
*Director of the United States Patent and Trademark Office*

*Attest:*

*Attesting Officer*